United States Patent [19]
Largeau et al.

[11] Patent Number: 5,631,383
[45] Date of Patent: May 20, 1997

[54] DERIVATIVES OF 2-AZABICYCLO[2.2.1] HEPTANE, THEIR PREPARATION AND THEIR APPLICATION

[75] Inventors: Denis Largeau, Taluyers; Patrick Leon, Tassin la Demi Lune, both of France

[73] Assignee: Rhone-Poulenc Rorer S.A., Antony, France

[21] Appl. No.: 476,156

[22] Filed: Jun. 7, 1995

[51] Int. Cl.$^6$ ................................. C07D 491/113
[52] U.S. Cl. ................ 548/430; 548/431; 548/434; 548/452; 548/512
[58] Field of Search .................... 548/452, 512, 548/430, 431, 434

[56] References Cited

U.S. PATENT DOCUMENTS

| | | | |
|---|---|---|---|
| 4,954,504 | 9/1990 | Chem et al. | 514/265 |
| 5,364,862 | 11/1994 | Spada et al. | 514/303 |

OTHER PUBLICATIONS

Reference Citation/Patent No. Chemical and Pharm. Bull., vol. 39, No. 5, 1991, (pp. 1112–1122), Author/Inventor or Assignee Katagiri, Muto, Nomura, Higashikawa, Kaneko, Patent/Publication Title Synthesis of Carbocyclic Nucleosides from 2-Azabicyclo[2.2.1]hept-5-en-3-ones: Sodium BorohydrideMediated Carbon-Nitrogen Bond.

Reference Citation/Patent No. Tetrahedron Letters, vol. 30, No. 13, 1989, pp. 1645–1648, Author/Inventor or Assignee Katagiri, Muto, Kaneko, Patent/Publication Title Stereospecific Synthesis of Carbocyclic Nucleosides from 2-Azabicyclo[2.2.1]Heptan-3-Ones Via Sodium Borohydride Mediated.

CA 95:151061h (±)-4β-Amino-... nucleosides. Cermak et al., p. 712, 1981.

CA 111:97692y Preparation ... inhibitors. Anton et al., p. 792, 1989.

CA 112:36336j Synthesis of ... cleavage. Katagiri et al., p. 630, 1990.

CA 117:171963e Adenosine analogs ... properties. Spada et al., p. 900, 1992.

*Primary Examiner*—Joseph McKane
*Attorney, Agent, or Firm*—Raymond S. Parker, III; R. Keith Baker; Martin F. Savitzky

[57] ABSTRACT

Novel derivatives of 1R- or 1S-2-azabicyclo[2.2.1]heptane with the general formula (I) or (I'), their preparation and their application;

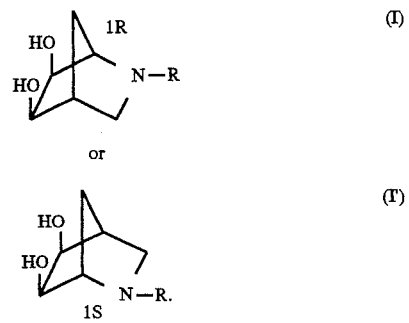

6 Claims, No Drawings

DERIVATIVES OF 2-AZABICYCLO[2.2.1] HEPTANE, THEIR PREPARATION AND THEIR APPLICATION

The present invention relates to novel derivatives of 1 R- or 1S-2-azabicyclo[2.2.1]heptane with the general formula

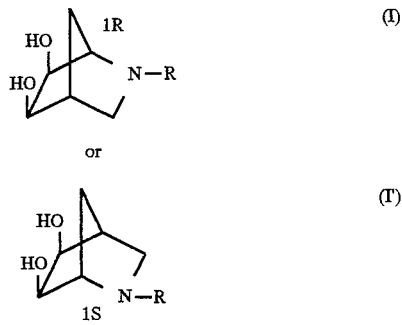

their preparation and their application.

In the general formulas (I) and (I'), R represents a hydrogen atom group or, respectively, a group with the general formula:

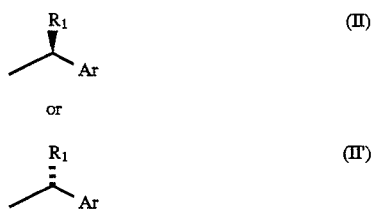

in which $R_1$ represents an alkyl group containing 1–4 carbon atoms and Ar represents a phenyl or α- or β-naphthyl group, optionally substituted by one or more identical or different atoms or groups selected from the halogen atoms and the alkyl groups containing 1–4 carbon atoms, alkoxy groups containing 1–4 carbon atoms, or nitro groups.

Preferably, $R_1$ represents a methyl or ethyl group, and Ar represents a phenyl group, which is optionally substituted by one or more methyl or methoxy groups.

Still more specifically, $R_1$ represents a methyl group, and Ar represents a phenyl group.

According to the invention, the products with the general formula (I) or (I') in which R represents, respectively, a group with the general formula (II) or (II') can be obtained by bis-hydroxylation of a product with the general formula:

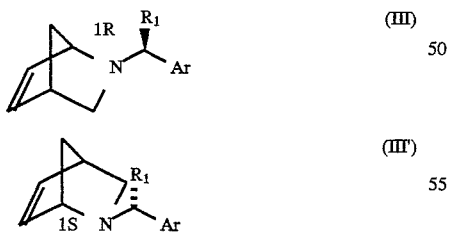

in which $R_1$ and Ar are defined as above.

In general, bis-hydroxylation is carried out by working under the conditions described by V. VanRheenen et al., Tetrahedron Letters, Vol. 23, 1973–1976 (1976). More particularly, the oxidation can be carried out by means of potassium permanganate or osmium tetroxide and working in the presence of N-methylmorpholine oxide or triethylamine oxide or potassium ferricyanide ($K_3FeCN_6$). In general, a mixture such as water-t-butanol or water-acetone is used as working aqueous-organic medium.

In general, the oxidant must be selected in such a manner that the 5,6-dihydroxy derivative is only formed in the exo form.

The product with the general formula (III) or (III') can be obtained by a Diels-Alder reaction between a homochiral amine with the general formula:

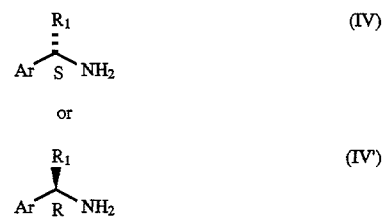

in which $R_1$ and Ar are defined as above, in the form of a salt, preferably with a mineral acid such as hydrochloric acid, formaldehyde and cyclopentadiene working under the conditions described by S. D. Larsen and P. A. Grieco, J. Amer. Chem. Soc., Vol. 107, 1768–1769 (1985).

The implementation of the method leads, starting from a homochiral amine with R- or S- form, to a mixture of 2 diastereoisomers which react in the same manner in the subsequent bis-hydroxylation step, and therefore do not necessarily have to be separated.

According to the invention, the product with the general formula (I) or (I') in which R represents a hydrogen atom can be obtained by hydrogenolysis of a product with the general formula (I) or (I'), in which R represents a group with the general formula (II) or (I') by means of hydrogen in the presence of a catalyst such as palladium on charcoal working in an organic solvent such as an alcohol, for example, methanol.

The novel products with the general formula (I) are particularly useful for the preparation of the products which are the object of U.S. Pat. No. 5,364,862 and which are active agents in the treatment of cardiovascular diseases, such as hypertension and myocardial ischemia.

[1 -S[1a,2b,3b,4a(S*)]]-4-[7-[[2-(3-chloro-2-thienyl]-1-ethylethyl]amino]-3H-imidazo[4,5-b]pyridin-3-yl]-N-ethyl-2,3-dihydroxycyclopentanecarboxamide of the following formula is of particular interest:

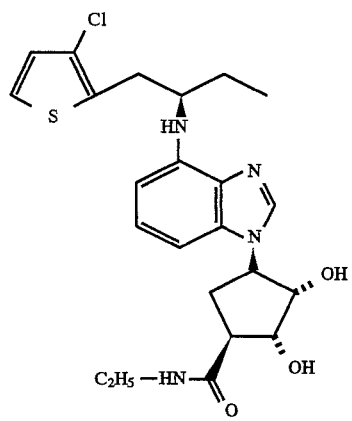

The products with the general formula (I) are particularly useful for the preparation of the carbo sugar with the general formula:

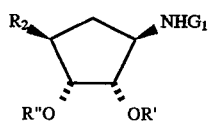

(V)

in which R2 represents carboxy, alkoxycarbonyl whose alkyl moiety contains 1-4 carbon atoms, N-alkylaminocarbonyl whose alkyl moiety contains 1-4 carbon atoms, or hydroxymethyl or alkoxymethyl, and R' and R", which may be identical or different, represent a hydrogen atom or an aliphatic organic acid residue containing 2-4 carbon atoms, such as an acetyl or propionyl or aromatic acid group such as a benzoyl residue, or R' and R" together form a methylene group whose carbon atom is optionally substituted by one or more groups, which may be identical or different, selected from the alkyl groups containing 1-4 carbon atoms, which can combine to form alicyclic group containing 5 or 6 carbon atoms, or phenyl groups, and G1 represents a hydrogen atom or a protecting group $G_2$ for the amino function. More particularly, R2 represents an ethylaminocarbonyl group or hydroxymethyl group, and R' and R" together form an isopropylidene group.

The carbo sugar with the general formula (V) constitutes one of the structural elements of the products claimed in U.S. Pat. No. 5,364,862.

The preparation of the carbo sugar with the general formula (V) from the product with the general formula (I) can be achieved as follows.

The hydroxy functions of the product with the general formula (I), in which R represents a hydrogen atom or a group with the general formula (II), can be protected in the form of an ester or acetal to yield a product with the general formula:

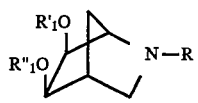

(VI)

in which R represents a hydrogen atom or a group with the general formula (II) and R'$_1$ and R"$_1$, which may be identical or different, represent an aliphatic organic acid residue containing 2-4 carbon atoms, such as an acetyl or propionyl group or an aromatic acid such as a benzoyl residue, or R'$_1$ and R"$_1$ together form a methylene group whose carbon atom is optionally substituted by one or more groups, which may be identical or different, selected from the alkyl groups containing 1-4 carbon atoms, which together can form an alicyclic group containing 5 or 6 carbon atoms, or phenyl groups.

In general, the protection of the hydroxy groups is achieved under the usual esterification or acetalization conditions, for example, by reacting acetic acid or propionic acid in the presence of p-toluenesulfonic acid in an organic solvent such as an aromatic hydrocarbon, for example, benzene or toluene, by separating the water gradually as it is formed or by reacting an aldehyde or a ketone, possibly in the form of an acetal, in the presence of an acid such as trifluoroacetic acid in an organic solvent such as an aromatic hydrocarbon, for example, benzene or toluene, at a temperature between 50° C. and the boiling point of the reaction mixture.

The product with the general formula (VI) in which R represents a group with the general formula (II) can be transformed into a product with the general formula (VI) in which R represents a hydrogen atom by hydrogenolysis.

In general, the hydrogenolysis is carried out by means of hydrogen, which is optionally pressurized, in the presence of a catalyst such as palladium on charcoal in an organic solvent such as an alcohol, for example, methanol, ethanol or isopropanol, at a temperature between 0° and 50° C.

The product with the general formula (VI), which is a model product, constitutes another subject of the present invention.

The product with the general formula (VI) in which R represents a hydrogen atom can be transformed into a product with the general formula:

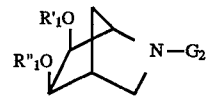

(VII)

in which R'$_1$ and R"$_1$ are defined as before and $G_2$ represents a protecting group for the amino function by a reaction with an appropriate reagent which allows the selective introduction of a protecting group.

The protecting groups are selected from those which can later be eliminated selectively. These protecting groups include the following, which are particularly well suited: the chloroacetyl, methoxymethyl, trichloro-2,2,2-ethoxycarbonyl, t-butyl, benzyl, p-nitrobenzyl, p-methoxybenzyl, diphenylmethyl, trialkylsilyl, allyloxycarbonyl, benzyloxycarbonyl groups, in which the phenyl ring is optionally substituted by a halogen atom or by an alkyl group containing 1-4 carbon atoms or alkoxy group containing 1-4 carbon atoms, or t-butoxycarbonyl. Among the protecting groups which are particularly well suited, one can mention those described by T. W. Greene and P. G. M. Wuis, "Protecting Groups in Organic Synthesis," Chapter 7, 2nd edition, John Wiley & Sons (1991).

The t-butoxycarbonyl group is of particular interest.

The product with the general formula (VII) in which $G_2$ represents a t-butoxycarbonyl group can be obtained directly from a product with the general formula (VI) in which R represents the group with the general formula (II) by simultaneous hydrogenolysis and t-butoxycarbonylation.

In general, the reaction is carried out by simultaneously reacting the hydrogen in the presence of a catalyst such as palladium and charcoal and di-t-butyl dicarbonate with a product with the general formula (VI) working in an organic solvent such as an alcohol, for example, methanol, ethanol or isopropanol, at a temperature between 0° and 50° C.

The product with the general formula (VII) is a novel product which constitutes another subject of the present invention.

The product with the general formula (VII) is then oxidized into a product with the general formula:

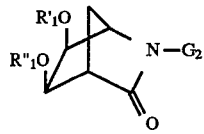

(VIII)

in which R'$_1$, R"$_1$ and $G_2$ are defined as above.

In general, the oxidation is conducted by means of a ruthenium oxide (RuO$_4$), which can be optionally generated in situ from a precursor such as RuO$_2$ or RuCl$_3$ in the presence of an oxidant selected from a periodate such as sodium periodate, a hypochlorate such as hypochlorite or sodium hypobromite or a bromate such as sodium bromate or an organic tertiary amine oxide such as N-methylmorpholine oxide or triethylamine oxide, working in water or in homogeneous or heterogeneous aqueous-organic medium, such as a water-ethyl acetate mixture.

The oxidation can also be conducted using sodium hypochlorite alone (javelle) or using potassium permanganate or sodium tungstate in the presence of an oxidant such as sodium hypochlorite, hydrogen peroxide or an alkyl hydroperoxide.

The product with the general formula (VIII) can also be obtained by oxidation of a product with the general formula (VI) in which R represents a hydrogen atom under the conditions described above, followed by the protection of the nitrogen atom of the lactam obtained with the general formula:

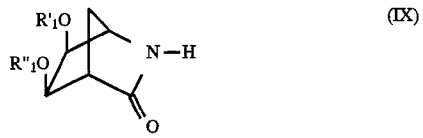

(IX)

in which $R'_1$ and $R''_1$ are defined as above, by a protecting group as defined above.

The product with the general formula (VIII) is a novel product which constitutes another subject of the present invention.

The product with the general formula (VIII) can be transformed into a product with the general formula (V) under conditions which are appropriate for the nature of the substituent R2 which must be introduced.

The product with the general formula (V) in which R2 represents a carboxy group can be prepared by reacting a mineral base such as sodium hydroxide with the product with the general formula (VIII), followed by the replacement of the protecting group $G_2$ by a hydrogen atom and optionally groups $R'_1$ and $R''_1$ by hydrogen atoms.

The product with the general formula (V) in which $R_2$ represents an alkoxycarbonyl group whose alkyl moiety contains 1–4 carbon atoms can be prepared by reacting an alcoholate of an alkali metal with the product with the general formula (VIII), followed by the replacement of the protecting group $G_2$ by a hydrogen atom and optionally of the groups $R'_1$ and $R''_1$ by hydrogen atoms.

The product with the general formula (V) in which $R_2$ represents an N-alkylaminocarbonyl group whose alkyl moiety contains 1–4 carbon atoms can be prepared by reacting an alkylamine with the product with the general formula (VIII), followed by the replacement of the protecting group $G_2$ by a hydrogen atom and optionally of the groups $R'_1$ and $R''_1$ by hydrogen atoms.

The product with the general formula (V) in which $R_2$ represents a hydroxymethyl group can be prepared by reacting a reducing agent such as a borohydride, for example, sodium or potassium borohydride, with the product with the general formula (VIII), followed by the replacement of the protecting group $G_2$ by a hydrogen atom and optionally of the groups $R'_1$ and $R''_1$ by hydrogen atoms.

The product with the general formula (V) can be used under the conditions described in U.S. Pat. No. 5,364,862 to produce the therapeutically active products.

The following examples illustrate the present invention.

EXAMPLE 1

Into a 250-cm³ three-necked flask equipped with a cooling apparatus and stirring system, a solution is introduced under an argon atmosphere, which solution consists of 20 g of a-S-methylbenzylamine (165 mmol) in 60 cm³ of water whose pH is adjusted to 6.10 by the addition of 17 cm³ of 36% hydrochloric acid (W/V). After cooling to 5° C., 20 cm³ of a 37% (W/V) aqueous formaldehyde solution are added. The solution is stirred for 5 minutes at 5° C.; then 21.8 g of cyclopentadiene (330 mmol) are added. The mixture is stirred for 16 h between −5° C. and 0° C. The aqueous phase is separated by decanting and then washed with 50 cm³ of pentane. The neutralization to pH=8.0 is achieved by addition of concentrated sodium hydroxide. Two extractions are then carried out, each with 70 cm³ of ethyl acetate. The pH of the aqueous phase is adjusted to 11 by the addition of concentrated sodium hydroxide, followed by two extractions, each with 70 cm³ of ethyl acetate. The organic phases are combined, and then washed two times with 50 cm³ of water, and then they are dried over sodium sulfate. After filtration and concentration to dryness at a reduced pressure, the yield consists of 33.10 g of -2-(α-S-methylbenzyl)-2-azabicyclo[2.2.1]hept-5-ene in the form of a slightly yellow oil.

Into a 500-cm³ three-necked flask equipped with a cooling apparatus and a stirring system, containing a solution of 20 g of 2-(α-S-methylbenzyl)-2-azabicyclo[2.2.1]hept-5-ene (75.34 mmol) in 220 cm³ of t-butanol, 12 g of N-methylmorpholine oxide in 32 cm³ of water, at a temperature of approximately 25° C., are added, then 6.3 cm³ of a 25% (W/V) solution of osmium tetroxide ($OsO_4$) in t-butanol are added slowly. The stirring is continued for 2 h at a temperature of approximately 20° C., then for 3 h at 65° C. After evaporation of the t-butanol at a reduced pressure, the residue is redissolved in 350 cm³ of isopropanol. After concentration to dryness at a reduced pressure, 24 g of cis-5,6-dihydroxy-2-(α-S-methylbenzyl)-2-azabicyclo [2.2.1]heptane are produced in the form of an oil. 14 g of 5R,6S-dihydroxy-2-(α-S-methylbenzyl)-2azabicyclo[2.2.1]heptane are produced by crystallization in cyclohexane, with an isomeric purity of more than 95%.

The NMR spectrum, determined in deuterochloroform, shows the following shifts (d): 1.21 (3H, d); 1.38 (1H, d); 1.59 (1H, d); 2.22 (2H, m); 2.45 (1H, dd); 2.95 (1H, s); 3.99 (1H, q); 3.78 (1H, d); 3.90 (1H, d); 7.28 (5H, m).

EXAMPLE 2

Into 500-cm³ three-necked flask, equipped with a cooling apparatus and a stirring system, containing a solution of 18.4 g of 5R,6S-dihydroxy-2-(α-S-methylbenzyl)-2-azabicyclo [2.2.1]heptane (76 mmol) in 130 cm³ of toluene, 31.7 g of 2,2-dimethoxypropane (304 mmol) and then 13 g of trifluoroacetic acid are added slowly (114 mmol). The mixture is heated for 4 h 10 minutes at 65° C. After cooling to 30° C. and concentration in the rotary evaporator to eliminate the toluene, the excess 2,2-dimethoxypropane and partially the trifluoroacetic acid, the reaction mixture is taken up in dichloromethane, then it is neutralized by the addition of 100 cm³ of 2N sodium hydroxide. After decanting, drying of the organic phase over sodium sulfate, filtration, treatment with decolorizing charcoal (30 g) for 30 minutes at the boiling point of dichloromethane, filtration through clarcel [possibly a trade name] and concentration to dryness at reduced pressure, the yield consists of 18.8 g of 5R,6S-isopropylidenedioxy-2-(α-S-methylbenzyl)-2-azabicyclo [2.2.1]heptane, whose structure is confirmed by the proton NMR spectrum, which, determined in deuterochloroform, shows the following shifts (d): 1.22 (3H, d); 1.23 (6H, s); 1.31 (1H, d); 1.57 (1H, d); 2.08 (1H, d); 2.34 (1H, broad s); 2.45 (1H, dd); 3.06 (1H, s); 3.40 (1H, q); 4.09 (1H, d); 4.19 (1H, d); 7.26 (5H, m).

In a 250-cm³ three-necked flask equipped with a stirring system, 0.5 g of 5% palladium on charcoal, 5 g of 5R,6S-isopropylidenedioxy-2-(α-S-methylbenzyl)-2-azabicyclo [2.2.1]heptane, 3.98 g of di-t-butyl dicarbonate and 36 cm³ of methanol. The apparatus is purged with argon and then with hydrogen, and then it is placed under a hydrogen atmosphere at 25° C. The reaction is continued for 5 h by carrying out a purge with hydrogen every 15 minutes to eliminate the carbon dioxide formed.

After filtration through clarcel and concentration to dryness at a reduced pressure, the yield consists of 4.84 g of 5R,6S-isopropylidenedioxy-2-(t-butoxycarbonyl)-2-azabicyclo[2.2.1]heptane, whose structure is confirmed by the NMR spectrum, which, determined in dimethyl sulfoxide-d6, shows the following chemical shifts (d): 1.16 (s, 3H); 1.28 (s, 3H); 1.32 (s, 1H); 1.34 (s, 3H); 1.65 (d, 1H); 2.38 (m, 1H); 2.65 (d, 1H); 2.99 (m, 1H); 3.84 (m, 1H); 3.94 (d, 1H); 4.16 (d, 1H).

In a 30-cm³ tube, 270 mg of 5R,6S-isopropylidenedioxy-2-(t-butoxycarbonyl)-2-azabicyclo[2.2.1]hepatane (1 mmol) and 40 mg of $RuO_2 \cdot H_2O$ (0.3 Eq) are introduced. 10 cm³ of ethyl acetate and 720 mg of water (40 Eq) are added. Then, 2.14 g of sodium periodate (10 Eq) are added, and the tube is sealed hermetically. The stirring is continued for 16 h at 50° C. The reaction mixture is filtered through clarcel, and then two extractions are carried out, each with 20 cm³ of ethyl acetate. The organic phases are dried over sodium sulfate. After the filtration and concentration to dryness at a reduced pressure, 245 mg of a solid are obtained, containing 68% of 5R,6S-isopropylidenedioxy-2-(t-butoxycarbonyl)-2-azabicyclo[2.2.1]heptan-3-one and 32% of starting material. The structure of the product obtained is confirmed by the NMR spectrum, which, determined in dimethyl sulfoxide $d_6$, shows the following chemical shifts (d): 1.38 (9H, s); 1.23 (3H, s); 1.33 (3H, s); 1.85 (1H, d); 1.93 (1H, d); 2.69 (1H, s); 4.24 (1H, s); 4.41 (1H, d); 4.51 (1H, d).

EXAMPLE 3

In a 25-cm³ autoclave, equipped with a magnetic stirrer, 1.47 g of 5R-6S-isopropylidenedioxy-2-(t-butoxycarbonyl)-2-azabicyclo[2.2.1]heptan-3-one in a solution in 10 cm³ of anhydrous toluene is introduced, followed by approximately 0.7 cm³ of ethylamine. The autoclave is closed and then heated at a temperature between 90° and 100° C. for 21 h. After cooling, the toluene is evaporated, and the dissolution is carried out with 10 cm³ of dichloromethane and 10 cm³ of water. After decanting, the organic phase is washed with 10 cm³ of water. The combined aqueous layers are washed in 10 cm³ of dichloromethane. The combined organic phases are washed with 10 cm³ of a saturated sodium chloride solution and then dried over sodium sulfate. After filtration and concentration to dryness at a reduced pressure, the yield consists of 1.58 g of a product containing 95% 2R,3S-isopropylidene-dioxy-4-R-t-butoxycarbonylam ino-1-S-ethylaminocarbonylcyclopentane, whose structure is confirmed by the NMR spectrum, which, determined in dimethyl sulfoxide-d6, shows the following chemical shifts: 0.95 (t, 3H); 1.14 (s, 3H); 1.31 (s, 12H); 1.55 (m, 1H); 2.11 (m, 1H); 2.64 (m, 1H); 3.00 (qi, 2H); 3.77 (m, 1H); 4.23 (m, 1H); 4.54 (m, 1H); 7.07 (d, 1H); 8.12 (t, 1H).

In a 25-cm³ flask, 1.22 g of 2R,3S-isopropylidenedioxy-4R-t-butoxycarbonylamino-1S-ethylaminocarbonylcyclopentane and 10 cm³ of dichloromethane are introduced. At a temperature of approximately 25° C., 0.85 g of trifluoroacetic acid is added with stirring. After 6 h of stirring and concentration to dryness, the yield consists of 1.16 g of 2R,3S-isopropylidenedioxy-4R-amino-1S-ethylaminocarbonylcyclopentane trifluoroacetate, whose structure is confirmed by the NMR spectrum, which, determined in dimethyl sulfoxide-d6, shows the following chemical shifts: 0.79 (t, 3H); 1.03 (s, 3H); 1.19 (s, 3H); 1.42 (m, 1H); 2.05 (m, 1H); 2.52 (m, 1H); 2.89 (qi, 2H); 3.04 (m, 1H); 4.16 (m, 1H

We claim:
1. A 1R- or 1S 2-azabicyclo [2.2.1]heptane compound of formula:

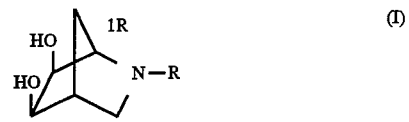

or

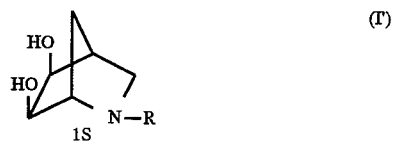

wherein R represents a hydrogen atom or, respectively, a group with the formula:

or

wherein $R_1$ represents an alkyl group containing 1–4 carbon atoms and Ar represents a phenyl or α- or β-naphthyl group, optionally substituted by one or more atoms or groups, which are identical or different, selected from halogen atoms, alkyl groups containing 1–4 carbon atoms, alkoxy groups containing 1–4 carbon atoms or a nitro group.

2. The compound according to claim 1 wherein $R_1$ represents a methyl or ethyl group and Ar represents a phenyl group, optionally substituted by one or more methyl or methoxy groups.

3. The compound according to claim 1 wherein $R_1$ represents a methyl group and Ar represents a phenyl group.

4. A compound of formula:

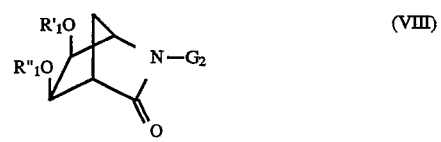

wherein $R'_1$ and $R''_1$, which are identical or different, represent an acyl group of an aliphatic organic acid containing 2–4 carbon atoms, or an aroyl group of an aromatic acid or $R'_1$ and $R''_1$ taken together form a methylene group whose carbon atom is optionally substituted by one or two groups, which are identical or different, selected from phenyl groups or alkyl groups containing 1 to 4 carbon atoms, or the alkyl groups taken together form an alicyclic group containing 5 or 6 carbon atoms, and $G_2$ represents a hydrogen atom or a protecting group for the nitrogen atom of the amido group of the compound.

5. A compound of formula:

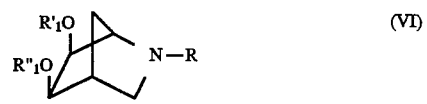

wherein R represents a h,ydrogen atom or a group with the general formula (II) as defined in claim 11 and $R'_1$ and $R''_1$, which are identical or different, represent an acyl group of an aliphatic organic acid containing 2–4 carbon atoms, or an aroyl group of an aromatic acid or $R'_1$ and $R''_1$ taken together form a methylene group whose carbon atom is optionally substituted by one or two groups, which are identical or different, selected from phenyl groups or alkyl groups containing 1 to 4 carbon atoms, or the alkyl groups taken together form an alicyclic group containing 5 or 6 carbon atoms.

6. A compound of formula:

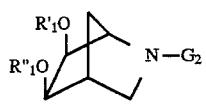 (VII)

wherein $R'_1$ and $R''_1$, which may be identical or different, represent an acyl group of an aliphatic organic acid containing 2–4 carbon atoms, or an aroyl group of an aromatic acid or $R'_1$ and $R''_1$ taken together form a methylene group whose carbon atom is optionally substituted by one or two groups, which are identical or different, selected from phenyl groups or alkyl groups containing 1 to 4 carbon atoms, or the alkyl groups taken together form an alicyclic group containing 5 or 6 carbon atoms, and $G_2$ represents a protecting group for the nitrogen atom of the amido group of the compound.

* * * * *